United States Patent [19]

Abramson

[11] 4,143,853
[45] Mar. 13, 1979

[54] VALVE FOR USE WITH A CATHETER OR THE LIKE

[75] Inventor: Harvey J. Abramson, New York, N.Y.

[73] Assignee: Metatech Corporation, Northbrook, Ill.

[21] Appl. No.: 815,598

[22] Filed: Jul. 14, 1977

[51] Int. Cl.² .............................................. F16K 37/28
[52] U.S. Cl. ............................... 251/149.1; 251/149.7; 137/515.7; 137/846; 128/274
[58] Field of Search ............ 128/349 BV, 350 V, 274; 137/846, 847, 848, 849, 515.7; 285/DIG. 22; 251/149.1, 149.2, 149.3, 149.4, 149.5, 149.6, 149.7

[56] References Cited

U.S. PATENT DOCUMENTS

| 584,091 | 6/1897 | Leidich | 251/149.2 |
| 996,588 | 6/1911 | Kennedy | 137/846 X |
| 3,572,375 | 3/1971 | Rosenberg | 137/515.7 X |
| 3,645,547 | 2/1972 | Glover | 285/DIG. 22 X |
| 3,710,942 | 1/1973 | Rosenberg | 137/846 X |

FOREIGN PATENT DOCUMENTS 737249  6/1966  Canada ...................................... 128/274

Primary Examiner—William R. Cline
Attorney, Agent, or Firm—Leydig, Voit, Osann, Mayer & Holt, Ltd.

[57] ABSTRACT

A miniature valve for use with a catheter or the like in which a cylindrical valve body is made up of a male member and female member telescoped together so as to define opposed annular seats surrounding a through-opening. A disc of rubber having a central domed portion containing an axial slit is mounted between the seats, the male and female members being detented so that the periphery of the disc is pinched thereby displacing rubber radially inwardly to keep the slit normally sealed against flow in either direction. The valve body has a female leur type connection adjacent the underside of the dome and a male leur type connection adjacent the top of the dome. The female connection is so spaced with respect to the disc that when a cooperating leur type male connector is inserted into the female connection the tip of the male connector engages the underside of the domed portion of the disc to open the slit to permit straight axial flow through the through-opening in either direction.

5 Claims, 8 Drawing Figures

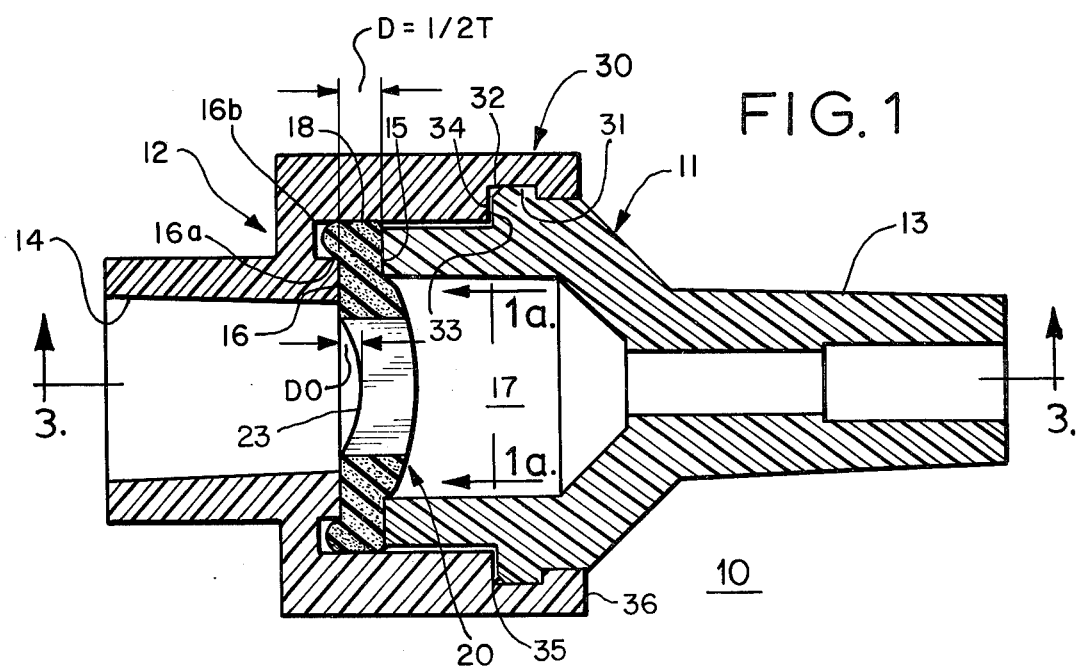
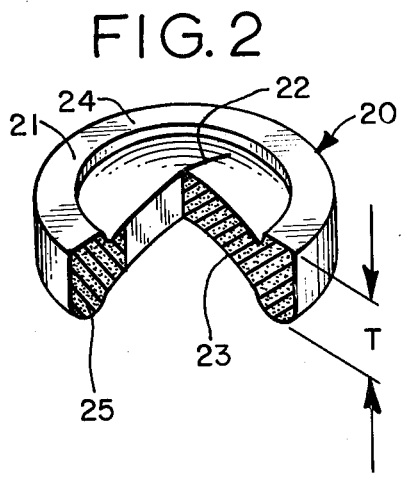
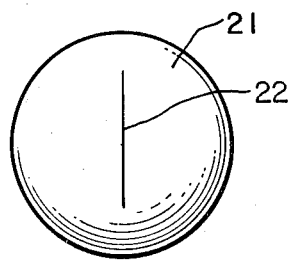
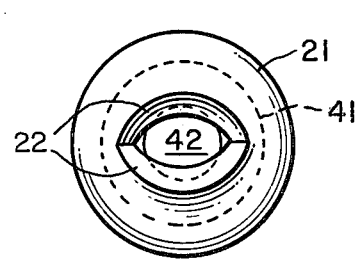
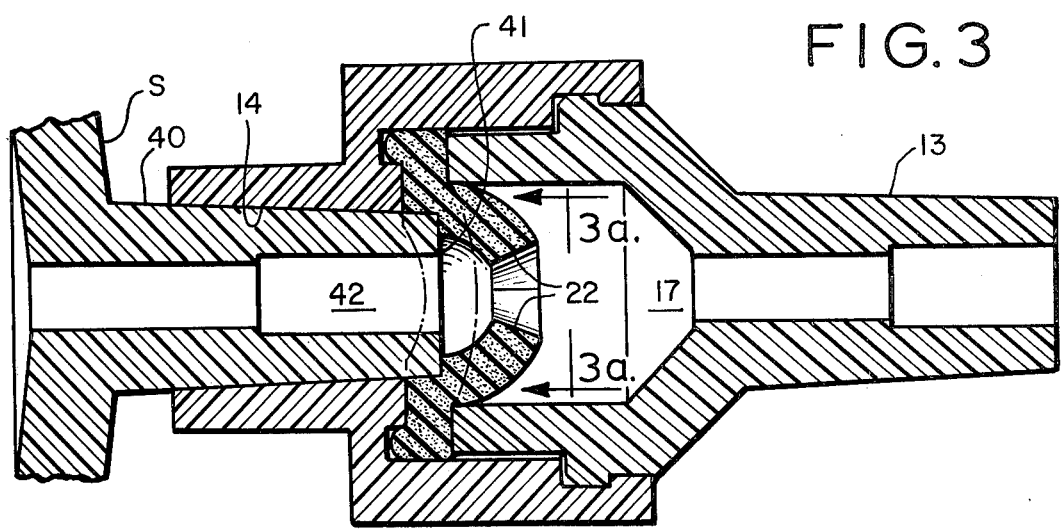

VALVE FOR USE WITH A CATHETER OR THE LIKE

In injecting fluids into the body or in withdrawal of fluids therefrom using a catheter, it is frequently desirable to provide a valve in the catheter which can be opened and closed at will. Such a valve should be capable of working reliably with either liquids or gases. In a typical usage the valve may be employed to seal in the air pumped into the cuff of an endotracheal tube. In another usage the valve may be permanently secured to an intravenous needle which is left in place in the patient and which permits a subsequent series of additions or withdrawals upon attachment of a standard syringe having a leur-type taper, the valve re-closing positively when the syringe is withdrawn.

A valve in common usage for such purpose is the so-called "Roberts" valve which is made up of an outer shell having an internal seat, a piston movable therein, a spring to bias the piston, and a sealing ring at the seat. When the piston is unseated to permit flow, the fluid must make two sharp 90° turns in traversing the valve. When the fluid is blood the turbulence induced by the 90° turns tends to cause precipitation or clotting which not only affects the quality of the blood but which increases the risk of clogging and malfunction of the valve; for example, the valve may fail to reseal itself when cutting off the flow.

It is an object of the present invention to provide a valve for use with a catheter or the like which is highly reliable in operation with all types of fluids, both liquid and gaseous, and which provides straight axial flow, free of 90° bends, for minimizing turbulence. It is therefore an object to provide a valve which is ideally suited to control of the flow of blood for minimizing the turbulence which causes sedimentation and clotting, which not only reduces the level of blood quality but which may cause clogging of the valve passageways.

It is another object of the present invention to provide a valve for use with a catheter or the like which is extremely simple in construction consisting of only three parts, telescoping male and female members and a soft rubber valve disc which is captured between them. It is a related object to provide a valve which is easily assembled requiring only the pressing together of the male and female members into a predetermined detented condition to achieve permanent assembly and to pre-stress the valve disc while guarding against any overstressing thereof.

It is another object of the invention to provide a catheter valve which may be manufactured economically without adherence to close tolerances but which is nonetheless capable of reliable usage on a universal basis with standard medical fittings of the leur type.

It is yet another object of the invention to provide a catheter valve which, although easily assembled, cannot be disassembled and therefore is tamper proof.

It is yet another object of the invention to provide a catheter valve which is highly sterile and which can be opened and closed as many times as desired, even in venous usage, without impairing its integrity. In this connection it is an object of the invention to provide a catheter valve which precludes leakage from the valve incident to opening and closing thereby preventing escape of fluid, particularly fluids such as blood which tend to form a dried accumulation which interferes with the operation of conventional valves. Indeed, in the present valve, any minor accumulation of blood or the like is limited to a film upon a rubber surface which is automatically dislodged by a flexing of the rubber the next time that the valve is operated.

Other objects and advantages of the valve will be apparent upon reading the attached detailed description and upon reference to the drawings in which:

FIG. 1 is an axial cross section of a valve constructed in accordance with the present invention and at a greatly enlarged scale.

FIG. 1a shows the slit in the rubber disc as viewed along line 1a—1a in FIG. 1.

FIG. 2 is a perspective view of the valve member in its relaxed state and in partial section.

FIG. 3 is an axial section showing the valve in open condition taken along line 3—3 of FIG. 1.

FIG. 3a is a view looking along line 3a—3a in FIG. 3 and showing the valve slit in its spread apart condition.

Figure 4:
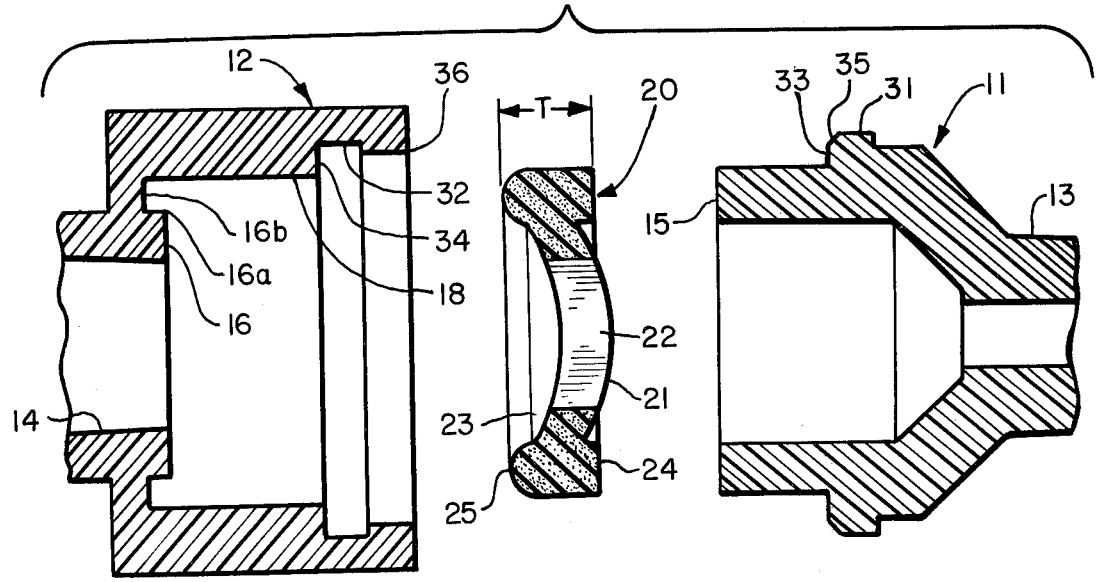
FIG. 4 is an exploded view of the valve elements.

While the invention has been described in connection with a preferred embodiment, it will be understood that I do not intend to be limited to the particular embodiment shown but intend, on the contrary, to cover the various alternative and equivalent forms of the invention included within the spirit and scope of the appended claims.

Turning now to FIGS. 1 and 2, there is shown, in cross section, a catheter valve 10 made up of a cylindrical male member 11 and a cylindrical female member 12. The male member has a male connection 13 having a standard leur-type taper and dimension while the member 12 has a leur-type female connection 14. The members, telescoped together, have respective internal annular seats 15, 16 opposed to one another and surrounding a central through-opening 17. The region of the opposed seats is bounded by a wall 18. Interposed between the seats is a valve disc 20 of soft rubber. The valve disc has a central domed portion 21 formed with a central, axially extending slit 22 which extends from the domed side through to the underside 23. The disc is bounded by a peripheral portion 24 which, in the relaxed state, has an axial dimension which is substantially greater than the average thickness of the domed portion 21. The peripheral portion is preferably of rounded cross section on its underside as indicated at 25. The disc is preferably made of a soft yet durable rubber having a durometer rating within the range of 35 to 45 on the Shore A scale.

While the valve is not limited to any particular size, it finds greatest utility with either leur-type or 15 millimeter taper fittings; the term "miniature" therefore includes a range of dimension. A typical valve disc intended for leur usage may have dimensions in the relaxed state as follows: diameter 7.4 millimeters, axial thickness of peripheral portion 1.9 millimeters and approximate thickness of domed portion 1.2 millimeters, with the surfaces of the domed portion having a radius of curvature on the order of 4.5 millimeters.

In carrying out the present invention the telescoping male and female members have axially engaging detent surfaces which snap into register as the members are telescoped together at a point where a substantial axial pinching force is developed in the periphery of the disc, that is, at the region which is engaged by the opposed seats 15, 16. The detent connection, indicated generally at 30, is formed by a shallow annular ridge 31 on the outside of the member 11 which engages with a shallow annular groove 32 formed on the inside of the member 12. The ridge and groove are so positioned that they snap into register when the clearance distance D between the opposed seats 15, 16 is one-half of the axial thickness T (see FIGS. 2 and 4) of the peripheral portion of the disc. While this ratio is not a critical one, nevertheless a sufficiently high pinching force should be developed in the peripheral portion of the disc so as to bring about a tight peripheral seal with the rubber being displaced or squeezed radially inwardly so that the domed portion 21 of the disc is placed under compression. This compressive force tends to press the sides of the slit 22 intimately together in order to keep the slit normally sealed against the flow of fluid in either direction. To further improve the efficacy of the peripheral seal, at least one of the annular seats if of a sharply stepped profile providing a concentrated line of stress on the disc. In the present instance the seat 16 has a step 16a defining an annular recess 16b, the latter serving, in addition, to accommodate some of the displaced rubber in order to avoid the building up of destructively high stress.

Figure 5:
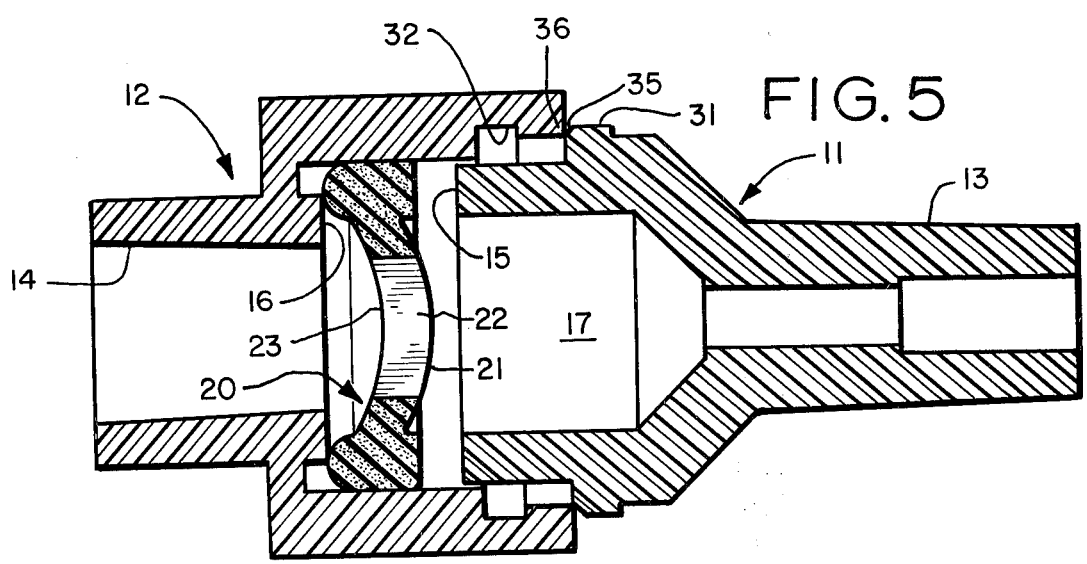
FIG. 5 illustrates the forcible telescoping of the members into assembled condition.

To insure that the axial pinching force at the periphery is translated into a precise degree of compression within the central or domed portion, the valve element is preferably made with a diameter, in the unstressed state, which coincides with the inner diameter of the member 12 (see FIG. 5).

Inter-engaging stop surfaces are, however, provided on the members 11, 12 in order to prevent overstress. Thus the member 11 has an annular stop surface 33 and the member 12 has a cooperating stop surface 34, which surfaces are respectively provided on the ridge and groove 31, 32 which form the detent. The stop surfaces 33, 34 come into bottoming engagement as the point of detenting is reached. Because of the interfering fit of the detent during assembly, at least one of the members is chamfered and at least one of the members is formed of resilient plastic so as to effect resilient cammed entry of the inner member 11 into the outer member 12. The chamfer, indicated at 35, is preferably formed on the leading edge of the ridge 31 so that the ridge cammingly clears the opposed leading edge 36 on the member 12. However, if desired, the edge 36 could be chamfered to perform the same function. Moreover, the valve, once assembled, cannot be disassembled, misadjusted, or tampered with in any way. It is one of the features of the invention, in any event, that once the members 11, 12 are pressed together in the assembled relation shown in FIG. 1, with snapping in place of the detent, the assembly cannot be taken apart and forms a disposeable unit.

In accordance with one of the important features of the present invention the female connection 14, on the member 12, is axially aligned with the disc 20 and adjacent the "underside" 23 of the dome portion of the disc and so spaced with respect thereto that when a cooperating male connector is inserted into the female connection 14, and pressed into tight seated condition, the tip of the male connection engages the domed portion of the disc to bow the same outwardly accompanied by spreading of the slit to permit axial flow of fluid through the through-opening 17. Thus, referring to FIG. 3, a typical leur-type male connector 40 is shown which may, for example, be the tip of a syringe S, having a presented tip 41 and a central passage 42. As the male connector 40 is pressed into its seated position, the tip 41 first engages and forms a sealing connection with the underside 23 of the disc. Upon advancing the male connector into its final seated position the tip presses inwardly upon the disc to bow it outwardly as illustrated in FIG. 3 accompanied by spreading of the slit so that a free passage is established between the conduits 17, 42 for passage of fluid in either direction.

As illustrated in FIG. 3a, the total unobstructed area of the opened slit 22 may, in a typical case, be substantially equal to the area of the conduit 42 in the male connector so that the valve does not produce a restriction in the flow or any substantial pressure drop.

Indeed, it is one of the primary features of the invention that a straight-through flow passage is provided between the conduit 42 and the through-opening 17 so that it is unnecessary for the fluid to make two or more abrupt 90° bends in traversing the valve. Thus the present valve is to be contrasted with the conventional Roberts valve in that the present valve minimizes turbulence and throttling of the fluid. Where the fluid being handled is blood, the lack of turbulence and throttling reduces any tendency toward sedimentation or clotting, in other words the high quality of the blood is maintained notwithstanding passage through the valve.

The dome-like nature of the center portion of the valve disc performs a number of different important functions. Preferably the "doming offset", indicated at DO in FIG. 1 is at least one-half of the clearance distance D between the seats which engage the disc periphery. Thus even a small amount of advancement of the tip 41 of the male connector 40 is capable of bringing about appreciable spreading of the slit. This is to be contrasted with use of a flat disc in which the initial effect of the bowing deformation is to wedge the underside edges of the slit even more tightly together just prior to the time that actual opening occurs.

A further advantage of the domed construction is that it prevents build-up of excessive compressive stress in the central portion of the disc by reason of the pinching at the periphery. In the event that excess compression tends to be developed at the center of the disc, the disc will accommodatingly bow, to very slight degree, in the axial direction; in other words, the excess compressive force has "somewhere to go" rather than meeting head on at the center of the disc.

A still further advantage of the domed construction is that the valve is capable of sealing extremely high pressures on the domed side. In short, the principle of the arch is utilized with the pressure on the domed side serving to seal the slit, under closed conditions, even more tightly. Such a high pressure condition is encountered where the valve is used to maintain a pumped up pressure in some mechanical device as, for example, the cuff of an endotracheal tube. The present valve, in such application, provides a positive seal against the slow leakage which tends to occur using check valves of more conventional construction.

Mention has already been made of the sequential sealing of the male connector against the surface of the rubber disc which is followed by opening of the valve upon entry. When the male connector 40 is withdrawn, the reverse sequence occurs: The initial portion of the withdrawal permits the slit to close. Only after the slit is closed, sealing off the flow, does the tip of the male connector leave the surface of the disc and thus break its sealing engagement.

The significance of this is that substantially no fluid is lost through the valve incident to opening it or closing it. This "no loss" characteristic is particularly important when handling blood and where repeated samples must be taken or repeated injections must be made through the same valve surfaces. In conventional valves each time the valve is opened and closed a small amount of blood is lost. This quickly dries in place and, the effect being cumulative, an encrustation may occur which may prevent the valve from re-sealing tightly, particularly where the valve, as in the case of the Roberts valve, utilizes the plunger principle. In the case of the present valve, not only is the amount of blood lost at each operation negligible but any dried accumulation which occurs on the resilient rubber surface of the valve member simply flexes with the rubber and cannot impede the valve motion. Thus the present valve may be used either intermittently or continuously over a long period of time without replacement and without compromising sterility.

Figure 6:
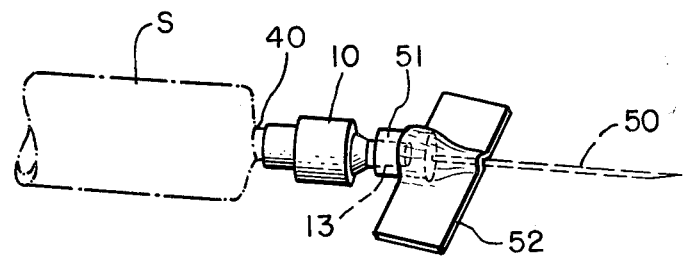
FIG. 6 illustrates a typical application of the valve in withdrawing a periodic blood sample and utilizing a hypodermic needle taped in position.

A typical usage of the valve in the taking of repeated blood samples using an implanted hypodermic needle is illustrated in FIG. 6. Here the needle, indicated at 50, having a leur-type female fitting 51 is shown inserted, as for example into a vein, and held in position by a strip 52 of adhesive tape. With the needle in place, leakage is prevented by the check valve action of the catheter valve 10. When it is desired to withdraw a blood sample, syringe S having a male connector 40 at its tip is simply inserted into the valve 10, with the tip of the connector serving to spread apart the slit in the valve element as discussed to provide direct, straight through communication with the needle 50. By applying vacuum within the syringe S, either mechanically or by using an evacuated syringe, a blood sample is promptly taken, following which the syringe is withdrawn and the valve 10 resiliently reseals itself until such time as the next sample may be required.

While the invention has been described in connection with a simple form of slit 22, the term "diametric slit" is not limited thereto and includes possible use of a three-legged or four-legged slit — the simple form of slit shown is, however, preferred. Also while the material of the valve element has been referred to as soft rubber, it will be understood that the term "rubber" is not limited to natural or synthetic rubber but includes rubber-like plastics having similar durometer characteristics.

While many types of plastics may be employed in molding the members which form the body of the present valve, the plastic which is chosen for the male member 11 should preferably have physical characteristics similar to acrylonitrile-butadiene-styrene (ABS) resin, and the plastic for the female member 12 should have characteristics similar to polypropylene.

While, in the preferred embodiment, the members 11, 12 are "doubly" male and female, respectively, this is not necessary in the practice of the invention and the terms "male" and "female" have significance primarily with respect to the female fluid connection which requires penetration for unseating of the valve surfaces.

What is claimed is:

1. A miniature valve for use with a catheter or the like comprising a cylindrical valve body made up of a cylindrical male member and a cylindrical female member telescoped together, the members having respective internal annular seats opposed to one another and surrounding a central through-opening, a disc of soft rubber having a central dome and having a peripheral portion substantially radially alined with the dome and axially interposed between the seats in a radially-confined position, the cylindrical members having interengaging means for holding them compressed together with the peripheral portion of the disc tightly pinched between the seats, the disc having a central axial slit, the pinching and radial confinement causing displacement of rubber radially inwardly to keep the slit normally sealed against fluid flow in either direction, the female member having a female connection axially alined with the disc and adjacent the concave side of the dome and so spaced with respect thereto that when a cooperating male connector is inserted into the female connection and pressed into tight seated condition, the tip of the male connector sealingly engages the dome of the disc to bow the same outwardly accompanied by spreading of the slit but short of penetration thereof to permit flow of fluid through the through-opening with resilient reclosure of the slit as the connector is subsequently withdrawn.

2. A miniature valve for use with a catheter or the like comprising a cylindrical valve body made up of a cylindrical male member and a cylindrical female member telescoped together, the members having respective internal annular seats opposed to one another and surrounding a central through-opening, the valve body having leur-type tapered male and female connections at the respective ends communicating with the through-opening, a disc of soft rubber having a diameter which snugly fills the space between the seats, the disc having a central domed portion of shallow dome shape and with a central axial slit, the axial dimension of the peripheral portion of the disc in the relaxed state being substantially greater than the average thickness of the domed portion, the male and female members having axially interengaging detent elements so positioned that when the members are detented together the peripheral portion of the rubber disc is tightly pinched between the seats accompanied by a radially inward displacement of rubber to stress the domed portion of the disc in radial compression thereby to keep the slit normally sealed against flow of fluid in either direction, the leur-type female connection being axially aligned with the disc and adjacent the concave side of the domed portion thereof and so spaced with respect thereto that when a cooperating leur-type male connector is inserted into the female connection and pressed into tight seated condition, the tip of the male connection sealingly engages the domed portion of the disc to bow the same outwardly accompanied by spreading of the slit but short of axial penetration thereby to permit axial flow of fluid through the through-opening.

3. A miniature valve for use with a catheter or the like comprising a cylindrical valve body made up of a cylindrical male member and a cylindrical female member telescoped together, the members having respective internal annular seats opposed to one another and surrounding a central through-opening, a disc of rubber having a diameter which snugly fills the space between the seats, the disc having a central domed portion of shallow dome shape and with a central axial slit, the male and female members having axially interengaging locking means so positioned that when the members are assembled together the peripheral portion of the rubber disc is pinched between the seats accompanied by a radially inward displacement of rubber to stress the central portion of the disc in compression thereby to keep the slit normally sealed against flow in either direction, the valve body providing a female connection axially alined with the disc and adjacent the concave side of of the domed portion thereof and so spaced with respect thereto that when a cooperating male connector is inserted into the female connection the tip of the male connection (a) first sealingly engages the concave side of the domed portion of the disc and (b) secondly bows the same outwardly thereby opening the slit to provide axial flow through the disc while maintaining the seal, and so that when the male connector is withdrawn the tip of the connector (c) first permits the slit to resiliently re-close and (d) secondly breaks the seal thereby to prevent leakage of fluid from the valve incident to the opening and closing thereof.

4. The combination as claimed in claim 3 in which the slit is centered in the disc and in which the length thereof is substantially shorter than the diameter of the domed portion of the disc.

5. A miniature valve for use with a catheter or the like comprising a cylindrical valve body made up of a cylindrical male member and a cylindrical female member telescoped together and having opposed annular seats, a disc of soft rubber having a central domed portion and a peripheral portion, the disc having a central diametrically extending axial slit, the male and female members having interengaging detent surfaces as well as stop surfaces so that when the members are telescoped together they snap into register at a point where the rubber is compressed up to about half of its normal axial dimension so that rubber is displaced radially inwardly to keep the slit normally sealed against fluid flow in either direction, the female member having a tapered female connection axially aligned with the disc and adjacent the underside of the dome so that when a cooperating male connector of mating taper is inserted into the female connection and pressed into tight seated condition the tip of the male connector engages the domed portion of the disc to bow the same outwardly but short of penetration thereof thereby spreading the slit to permit flow of fluid through the valve body with resilient closure of the slit as the connector is subsequently withdrawn, the rubber forming the disc having a durometer rating within the range of approximately 35 to 45 on the Shore A scale.

* * * * *